(12) United States Patent
Uno et al.

(10) Patent No.: US 6,197,918 B1
(45) Date of Patent: Mar. 6, 2001

(54) METHOD FOR MANUFACTURING AROMATIC CARBONATES

(75) Inventors: Kazutoyo Uno, Chiba; Masahide Tanaka; Tomoaki Shimoda, both of Ichihara, all of (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/458,277

(22) Filed: Dec. 9, 1999

(30) Foreign Application Priority Data

Dec. 25, 1998 (JP) .................................. 10-370370

(51) Int. Cl.[7] .................................................. C08G 64/00
(52) U.S. Cl. .................................... 528/196; 528/198
(58) Field of Search ...................... 528/196, 198

(56) References Cited

U.S. PATENT DOCUMENTS 5,210,268   5/1993   Fukuoka et al. ..................... 558/270
5,760,156   6/1998   Inoki et al. ........................... 528/67

FOREIGN PATENT DOCUMENTS 780 361     12/1996   (EP) .
3291257     12/1991   (JP) .
9165357     6/1997    (JP) .
9165443     6/1997    (JP) .

Primary Examiner—Terressa M. Boykin

(57) ABSTRACT

The present invention provides a method, which makes it possible to manufacture aromatic carbonates from dialkyl carbonates and aromatic hydroxy compounds inexpensively and with good efficiency. The method uses a titanium catalyst in a particular amount relative to aromatic polyhydric hydroxy compound impurities in a crude aromatic hydroxy compound solution.

7 Claims, 1 Drawing Sheet

METHOD FOR MANUFACTURING AROMATIC CARBONATES

BACKGROUND OF THE INVENTION

The present application is a U.S. non-provisional application based upon and claiming priority from Japanese Application No. HEI 10-370370, which is hereby incorporated by reference.

The present invention concerns a method for manufacturing aromatic carbonates, and specifically concerns a method for manufacturing aromatic carbonates which makes it possible to manufacture aromatic carbonates efficiently and inexpensively from dialkyl carbonates and aromatic hydroxy compounds.

Diphenyl carbonate (DPC) is a compound that is industrially useful as a raw material for the manufacture of polycarbonates, etc. Accordingly, the manufacture of aromatic carbonates with good productivity has great industrial value.

It has long been known that diaryl carbonates such as diphenyl carbonate, etc., can be obtained by reacting dialkyl carbonates with aromatic hydroxy compounds.

For example, when dimethyl carbonate and phenol are reacted, methylphenyl carbonate, diphenyl carbonate or a mixture of both compounds is obtained as shown below.

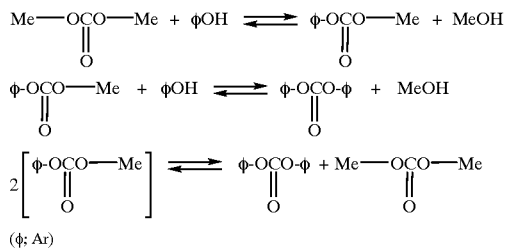

However, the above reactions are all equilibrium reactions, and the rates of these reactions are slow.

Various types of catalysts, which for example increase the reaction rate, have been proposed as means of solving such a problem.

Furthermore, attempts have also been made to separate alcohols such as methyl alcohol, etc., produced as by-products in the reaction from the raw materials, product or solvent, and to distill such alcohols away so that the reaction is caused to proceed to the product system side, and the use of reactors with attached distillation columns is also known.

Furthermore, a method for the continuous manufacture of aromatic carbonates in which a continuous multi-stage distillation column is used, and alcohols, etc., produced as by-products by the reaction are continuously removed from the system by distillation, so that the reaction product can be continuously led out of the system while causing the reaction to proceed to the product system side, has been proposed in Japanese Laid-Open Patent Application (Kokai) No. Hei 3-291257.

In the case of such a reaction, it is known that alkyl aromatic ethers are produced as by-products in addition to the aromatic carbonate constituting the intended product. For example, it is known that anisole is produced as a by-product according to the following formula when dimethyl carbonate is reacted with phenol.

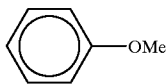

It is thought that this anisole is produced as a result of a de-carbonic acid reaction of methylphenyl carbonate with the reaction product of dimethyl carbonate and phenol. If the reaction of dimethyl carbonate and phenol is performed at a high temperature in order to increase the production efficiency of the aromatic carbonate, the production rate of anisole increases.

Accordingly, in Japanese Laid-Open Patent Application (Kokai) No. Hei 9-165357, the present inventors discovered that aromatic carbonates can be manufactured with good productivity and with little production of alkyl aromatic ethers as by-products by reacting dialkyl carbonates and aromatic polyhydric hydroxy compounds under specified conditions, and such a manufacturing process was proposed.

In cases where polycarbonates are manufactured by means of a melt polycondensation reaction using such aromatic hydroxy compounds, aromatic hydroxy compounds are also produced as by-products. If aromatic carbonates are manufactured by reusing such by-product aromatic hydroxy compounds as raw materials, the manufacturing cost of such aromatic carbonates can be lowered, so that the inexpensive manufacture of aromatic carbonates may be expected.

In Japanese Laid-Open Patent Application (Kokai) No. 9-165443, the present inventors proposed the inexpensive manufacture of polycarbonates by recycling and reusing aromatic hydroxy compounds produced as by-products during polycarbonate manufacture in a diaryl carbonate manufacturing process.

However, in this method as well, purification of the by-product aromatic hydroxy compounds was necessary, so that the results were not always satisfactory.

When the present inventors conducted research in light of the above-mentioned prior art, the inventors discovered that even if crude aromatic hydroxy compounds containing aromatic polyhydric hydroxy compounds are used, aromatic carbonates can be manufactured by using a Lewis acid containing titanium atoms as a catalyst, and setting the molar ratio of the catalyst to aromatic polyhydric hydroxy compounds contained as impurities at a specified ratio. This discovery led to the perfection of the present invention.

BRIEF SUMMARY OF THE INVENTION

The present invention was devised on the basis of the above-mentioned research. The object of the present invention is to provide a method, which makes it possible to manufacture aromatic carbonates efficiently and inexpensively from dialkyl carbonates and aromatic hydroxy compounds.

The method of the present invention for manufacturing aromatic carbonates is characterized by the fact that in a case where aromatic carbonates are manufactured while by-product alcohols and by-product dialkyl carbonates are distilled from the reaction system following the reaction of a dialkyl carbonate and an aromatic hydroxy compound in the presence of a catalyst, (i) a crude aromatic hydroxy compound which contains an aromatic hydroxy compound and a small amount of an aromatic polyhydric hydroxy compound is used, (ii) a titanium compound expressed by $TiX_3$ or $TiX_4$ (here, X indicates a halogen atom, an acetoxy group, an alkoxy group or an aryloxy group) is used as the catalyst, and (iii) when the catalyst is calculated in terms of titanium atoms, the amount of catalyst used is an amount that satisfies the following relationship with respect to the aromatic polyhydric hydroxy compound contained in the aromatic hydroxy compound:

aromatic polyhydric hydroxy compound/titanium atoms (molar ratio) >2.

It is desirable that the amount of the aromatic polyhydric hydroxy compound that is contained in the crude aromatic hydroxy compound be in the range of 0.5 to 10 wt %.

Furthermore, it is desirable that the aromatic hydroxy compound be phenol.

Furthermore, it is desirable that the aromatic polyhydric hydroxy compound be bisphenol A.

Moreover, it is desirable that compounds obtained by purifying the aromatic hydroxy compounds produced as by-products in the manufacture of a polycarbonate be used as the above-mentioned crude aromatic hydroxy compound.

DETAILED DESCRIPTION OF THE INVENTION

Below, the method of the present invention for manufacturing aromatic carbonates will be described in concrete terms.

In the method of the present invention for manufacturing aromatic carbonates, when alkylaryl carbonates, diaryl carbonates or aromatic carbonates consisting of mixtures of both types of carbonates are manufactured while by-product alcohols and by-product dialkyl carbonates are distilled away from the reaction system following the reaction of dialkyl carbonates with aromatic hydroxy compounds in the presence of a catalyst, the reaction is performed under specified conditions which will be described later.

Raw Materials

First, the dialkyl carbonates and aromatic hydroxy compounds that are used as raw materials when aromatic carbonates are manufactured in the present invention will be described.

Dialkyl Carbonates

Dialkyl carbonates expressed by the following general formula (i) are used in the present invention.

   (i)

($R^1$ and $R^2$ indicate alkyl groups, alkenyl groups, alicyclic groups or aralkyl groups; $R^1$ and $R^2$ may be the same or different, and $R^1$ and $R^2$ may form a ring together.)

Concrete examples of $R^1$ and $R^2$ include alkyl groups such as methyl groups, ethyl groups, propyl groups, butyl groups, pentyl groups, hexyl groups, heptyl groups, octyl groups, nonyl groups and decyl groups, etc., alkenyl groups such as allyl groups and butenyl groups, etc., alicyclic groups such as cyclopropyl groups, cyclobutyl groups, cyclopentyl groups, cyclohexyl groups and cycloheptyl groups, etc., alkyl groups containing alicyclic groups such as cyclohexylmethyl groups, etc., and aralkyl groups such as benzyl groups, phenethyl groups, phenylpropyl groups, phenylbutyl groups and methylbenzyl groups, etc.

Furthermore, these groups may be substituted by lower alkyl groups, lower alkoxy groups, cyano groups or halogens, and may also contain unsaturated bonds.

Examples of such dialkyl carbonates expressed by general formula (i) include dimethyl carbonate, diethyl carbonate, dipropyl carbonate, diallyl carbonate, dibutenyl carbonate, dibutyl carbonate, dipentyl carbonate, dihexyl carbonate, diheptyl carbonate, dioctyl carbonate, dinonyl carbonate, didecyl carbonate, methylethyl carbonate, methylpropyl carbonate, methylbutyl carbonate, ethylpropyl carbonate, ethylbutyl carbonate, ethylene carbonate, propylene carbonate, di(methoxymethyl) carbonate, di(methoxyethyl) carbonate, di(chloroethyl) carbonate, di(cyanoethyl) carbonate, dicyclopentyl carbonate, dicyclohexyl carbonate, dicycloheptyl carbonate, dibenzyl carbonate, diphenethyl carbonate, di(phenylpropyl) carbonate, di(phenylbutyl) carbonate, di(chlorobenzyl) carbonate and di(methoxybenzyl) carbonate, etc.

These compounds may also be used in combinations consisting of two or more compounds.

Among these compounds, dialkyl carbonates in which $R^1$ and $R^2$ respectively consist of alkyl groups with 4 or fewer carbon atoms are desirable. Furthermore, dimethyl carbonate and diethyl carbonate are even more desirable, and dimethyl carbonate is especially desirable.

Aromatic Hydroxy Compounds

The aromatic hydroxy compounds used in the manufacture of aromatic carbonates are expressed by the following general formula (ii):

$$Ar^1OH \qquad\qquad\qquad (ii)$$

$Ar^1$ indicates a monovalent aromatic group; this aromatic group may also have substituent groups.

Examples of such aromatic hydroxy compounds include phenol, cresol, xylenol and alkylphenols such as trimethylphenol, tetramethylphenol, ethylphenol, propylphenol, butylphenol, diethylphenol, methylethylphenol, methylpropylphenol, dipropylphenol, methylbutylphenol, pentylphenol, hexylphenol and cyclohexylphenol, etc., and alkoxyphenols such as methoxyphenol and ethoxyphenol, etc. and, as well as naphthol and substituted naphthols.

Substituted phenols expressed by

A indicates a divalent group, e.g., ——O——, ——S——, ——CO——, ——$SO_2$——, a (substituted) alkylene group expressed by

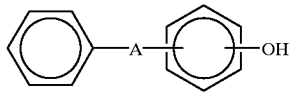

or a cycloalkylene group such as

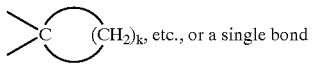, etc., or a single bond (Here, $R^4$, $R^5$, $R^6$ and $R^7$ each indicate a hydrogen atom, lower alkyl groups, cycloalkyl group, aryl group or aralkyl group, and these groups may be substituted by halogen atoms or alkoxy groups. Furthermore, k is an integer from 3 to 11, and the hydrogen atoms may be substituted by lower alkyl groups, aryl groups or halogen atoms, etc.

Furthermore, the aromatic rings may be substituted by substituent groups such as lower alkyl groups, lower alkoxy groups, ester groups, hydroxyl groups, nitro groups, halogens or cyano groups, etc.

Hetero-aromatic hydroxy compounds such as hydroxypyridine, hydroxycoumarin and hydroxyquinoline, etc., may be cited as examples.

In the present invention, among the above-mentioned compounds, monohydroxy compounds in which $Ar^1$ in the above-mentioned formula (ii) consists of an aromatic group with 6 to 10 carbon atoms are desirable, phenol, m- and/or p-cresol are more desirable, and phenol is especially desirable. Furthermore, such aromatic hydroxy compounds may be used in combinations consisting of two or more compounds.

In the method of the present invention for manufacturing aromatic carbonates, crude aromatic hydroxy compounds, which contain small amounts of aromatic polyhydric hydroxy compounds along with the above-mentioned aromatic hydroxy compounds are used.

Such crude aromatic hydroxy compounds contain aromatic polyhydric hydroxy compounds as impurities. Examples of aromatic polyhydric hydroxy compounds contained in such crude aromatic hydroxy compounds include hydroquinone, resorcin, catechol, dihydroxynapthalene, dihydroxyanthracene, alkyl-substituted forms of these compounds, and aromatic dihydroxy compounds expressed by the following formula (iv), etc.

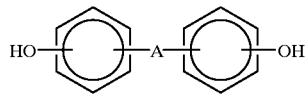

(iv)

(A is the same as the above-mentioned A, and the aromatic rings may be substituted by substituent groups such as lower alkyl groups, lower alkoxy groups, ester groups, hydroxyl groups, nitro groups, halogens or cyano groups, etc.)

Aromatic dihydroxy compounds expressed by formula (iv) are desirable as the above-mentioned aromatic polyhydric hydroxy compounds contained as impurities, and bisphenol A is especially desirable as such a compound.

It is desirable that such aromatic polyhydric hydroxy compounds be contained in the crude aromatic hydroxy compound at the rate of 0.5 to 10 wt %, preferably 0.5 to 2.0 wt %.

Furthermore, in addition to the above-mentioned aromatic polyhydric hydroxy compounds, the crude aromatic hydroxy compound may also contain aromatic polyhydric hydroxy compounds that contain ether groups, etc.

In the present invention, compounds obtained by purifying the aromatic hydroxy compounds produced as by-products when aromatic polycarbonates are manufactured by subjecting aromatic carbonates and aromatic polyhydric hydroxy compounds to a melt polycondensation reaction as indicated by the formula shown below may be used as the above-mentioned crude aromatic hydroxy compound.

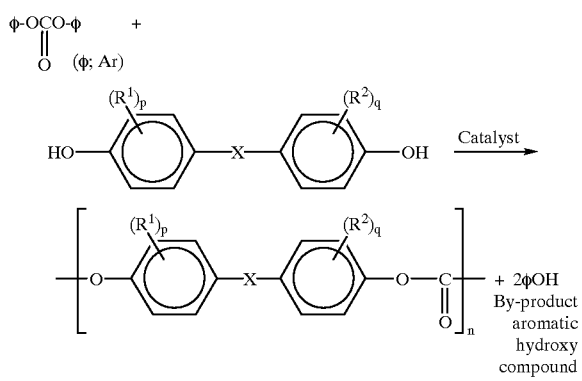

In the above formula, $R^1$ and $R^2$ are halogen atoms or monovalent hydrocarbon groups which may be substituted by halogens. These groups may be the same or different p and q are integers from 0 to 4 which indicate respective numbers of substituent groups. In cases where p or q is 2 or greater, the respective $R^1$ groups or the respective $R^2$ groups may be the same or different.

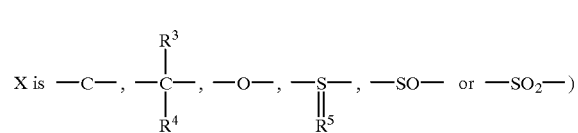

In the above-mentioned reaction, a universally known nitrogen-containing basic compound is ordinarily used as a catalyst. A catalyst of this type is used at the rate of $1\times10^{-6}$ to $1\times10^{-1}$ moles, preferably $1\times10^{-5}$ to $1\times10^{-2}$ moles, per mole of the above-mentioned aromatic polyhydric hydroxy compound. Furthermore, alkali metal compounds (or alkaline earth metal compounds) and/or boric acid compounds may be used along with nitrogen-containing basic compounds as catalysts.

Such aromatic hydroxy compounds produced as by-products during the manufacture of polycarbonates can be purified by ordinary methods such as distillation, etc., so that the catalytic components are separated and removed.

Furthermore, catalytic components can also be removed by adsorption using an ion exchange resin or a solid acid such as active clay, etc.

It is desirable that a nitrogen-containing basic compound be present at the rate of $1\times10^4$ moles or less, preferably 1×10–5 moles or less, in a crude aromatic hydroxy compound purified in this manner.

When aromatic carbonates are manufactured using a crude aromatic hydroxy compound in which the amount of nitrogen-containing basic compound is thus decreased, the rate of production of alkyl aromatic ethers such as anisole, etc., can be kept to a low rate.

Accordingly, polycarbonates can be manufactured by effectively utilizing aromatic hydroxy compounds produced as by-products in a polycarbonate manufacturing process, and the productivity of such polycarbonates can be improved.

Manufacture of Aromatic Carbonates

In the present invention, aromatic carbonates are manufactured by means of the reaction shown below from the above-mentioned dialkyl carbonates and aromatic hydroxy compounds. Below, furthermore, a case will be described in which dialkyl carbonates in which $R^1$ and $R^2$ in the above-mentioned formula (i) are the same are used as aromatic carbonates.

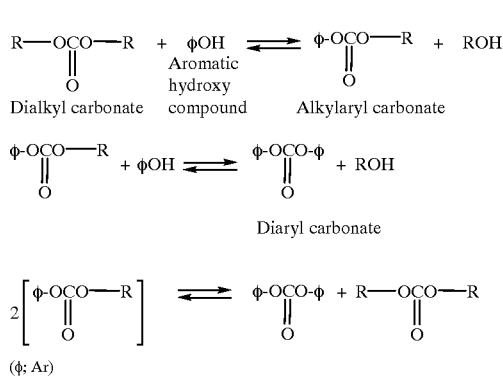

Concrete examples of alkylaryl carbonates which can be obtained by the above-mentioned reaction (1) include methylphenyl carbonate, ethylphenyl carbonate, propylphenyl carbonate, allylphenyl carbonate, butylphenyl carbonate, pentylphenyl carbonate, hexylphenyl carbonate, heptylphenyl carbonate, octyltolyl carbonate, nonyl(ethylphenyl) carbonate, decyl(butylphenyl) carbonate, methyltolyl carbonate, ethyltolyl carbonate, propyltolyl carbonate, butyltolyl carbonate, allyltolyl carbonate, ethylxylyl carbonate, methyl(trimethylphenyl) carbonate, methyl (chlorophenyl) carbonate, methyl(nitrophenyl) carbonate, methyl(methoxyphenyl) carbonate, methylcumyl carbonate, methyl(naphthyl) carbonate, methyl(pyridyl) carbonate, ethylcumyl carbonate, methyl(benzoyl phenyl) carbonate, ethylxylyl carbonate, benzylxylyl carbonate, methyl (hydroxyphenyl) carbonate, ethyl(hydroxyphenyl) carbonate, methoxycarbonyloxybiphenyl, methyl (hydroxybiphenyl) carbonate, methyl-2-(hydroxyphenyl) propylphenyl carbonate and ethyl-2(hydroxyphenyl) propylphenyl carbonate, etc.

Furthermore, concrete examples of diary compounds which can be obtained by the above-mentioned reactions (2) and (3) include diphenyl carbonate, ditolyl carbonate, phenyltolyl carbonate, di(ethylphenyl) carbonate, phenyl (ethylphenyl) carbonate, dinaphthyl carbonate, di(hydroxyphenyl) carbonate and di[2-(hydroxyphenylpropyl)phenyl] carbonate, etc.

Furthermore, the above examples also include cases in which aromatic polyhydric hydroxy compounds are used as aromatic hydroxy compounds.

Aromatic carbonates which can be manufactured in the present invention include the above-mentioned alkylaryl carbonate, diaryl carbonate and mixtures of both types of carbonates. Diaryl carbonate is especially desirable.

In the present invention, it is desirable to use raw materials which are such that alcohols having a lower boiling point than the aromatic carbonate reaction product are produced as by-products in the above-mentioned reaction, so that the aromatic carbonate can be led out from the bottom of the reaction column, while the by-product alcohols are led out from the top of the reaction column. To cite concrete examples of raw materials, methylphenyl carbonate is desirable as an alkylaryl carbonate, while diphenyl carbonate is desirable as a diaryl carbonate.

The reaction of such dialkyl carbonate and aromatic hydroxy compounds is ordinarily performed in a liquid state in the presence of a catalyst.

Lewis acids expressed by $TiX_3$ or $TiX_4$ (here, X indicates a halogen atom, acetoxy group, alkoxy group or aryloxy group) are used as catalysts.

Concrete examples of such titanium compounds include titanium tetrachloride, tetraphenoxytitanium $(Ti(OPh)_4)$, tetracresoxytitanium, tetramethoxytitanium $(Ti(OMe)_4)$, tetraethoxytitanium, tetraisopropoxytitanium and tetradodecyloxytitanium, etc.

Such titanium compounds may be compounds that will dissolve in the reaction solution under the reaction conditions (homogeneous system), or compounds that will not dissolve in the reaction solution (heterogeneous system).

Furthermore, for example, Lewis acids, tin compounds, lead compounds, copper group metallic compounds, alkali metal complexes, zinc complexes, iron group metallic compounds, zirconium complexes or solid catalysts, etc., may also be used in combination with the above-mentioned titanium compounds as catalysts. In concrete terms, examples of Lewis acids that can be used include Lewis acids and transition metal compounds that generate Lewis acids such as $AlX_3$, $VOX_3$, $VX_5$, $ZnX_2$, $FeX_3$ and $SnX_4$ (here, X indicates a halogen atom, acetoxy group, alkoxy group or aryloxy group), etc. Concrete examples of such compounds include tetraisooctyloxytin and triisopropoxyaluminum, etc.

Examples of tin compounds that can be used include organo-tin compounds such as trimethyltin acetate, triethyltin acetate, tributyltin acetate, triphenyltin acetate, dibutyltin diacetate, dibutyltin dilaurate, dioctyltin dilaurate, dibutyltin adipinate, dibutyldimethoxytin, dibutyldiphenoxytin, $[Bu_2Sn(OPh)]_2O$, dimethyltin glycolate, dibutyldiethoxytin, triethyltin hydroxide, hexaethyltannoxane, hexabutylstannoxane, dibutyltin oxide (Bu2SnO), dioctyltin oxide, butyltin triisooctylate, octyltin triisooctylate, butylstannic acid, octylstannic acid, polymer-form tin compounds such as poly[oxy(dibutylstannylene)], etc., and polymer-form hydroxystannoxanes such as poly (ethylhydroxystannoxane), etc. In addition, tin oxide may also be used.

Examples of lead compounds that can be used include lead oxides such as PbO, $PbO_2$ and $Pb_3O_4$, etc., lead sulfides such as PbS and $Pb_2S$, etc., lead hydroxides such as $Pb(OH)_2$ and $Pb_2O_2(OH)_2$, etc., plumbites such as $Na_2PbO_2$, $K_2PbO_2$, $NaHPbO_2$ and $KHPbO_2$, etc., plumbates such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$, etc., lead carbonates and basic salts of the same such as $PbCO_3$, $2PbCO_3Pb(OH)_2$, etc., lead salts of organic acids, as well as lead carbonates and basic salts of the same, such as $Pb(OCOCH_3)_2$, $Pb(OCOCH_3)_4$ and $Pb(OCOCH_3)_2$ $PbO3H_2O$, etc., organo-lead compounds such as $R_4Pb$, $R_3PbCl$, $R_3PbBr$, $R_3Pb$, $R_6Pb_2$, $R3PbOH$ or $R_3PbO$ (here, R indicates an alkyl group such as $C_4H_9$, etc., or an aryl group such as a phenyl group, etc.), alkoxylead compounds or aryloxylead compounds such as $Pb(OCH_3)_2$, $(CH_3O)Pb$ $(OPh)$ or $Pb(OPh)_2$, etc., lead alloys such as Pb-Na, Pb-Central attachment part (18), Pb-Ba, Pb-Sn or Pb-Spring bushing (22), etc., lead ores such as galena or zincblende, etc., and hydrates of these lead compounds, etc.

Examples of copper group metal compounds which can be used include salts and complexes of copper group metals such as CuCl, $CuCl_{12}$, CuBr, $CuBr_2$, CuI, $CuI_2$, $Cu(OAc)_2$, $Cu(acac)_2$, copper olefinates, $Bu_2Cu$, $(CH_3O)_2Cu$, $AgNO_3$, AgBr, silver picrate, $AgC_6H_6ClO_4Ag$ (bulvalene[?])$_3NO_3$ or $[AuC\equiv C-C(CH_3)_3]_n[Cu(C_7H_8)Cl]_4$, etc. (here, acac indicates an acetylacetone chelate ligand).

Examples of alkali metal complexes which can be used include Li(acac) and $LiN(C_4H_9)_2$, etc.

Examples of zinc complexes which can be used include $Zn(acac)_2$, etc.

Examples of cadmium complexes which can be used include $Cd(acac)_2$, etc.

Examples of iron group metal compounds which can be used include $Fe(C_{10}H_8)(CO)_5$, $Fe(CO)_5$, $Co(C_5F_6)(CO)_7$, $Ni-C_5H_5NO$ and ferrocene, etc.

Examples of zirconium complexes which can be used include $Zr(acac)_4$ and zirconocene, etc.

Examples of solid catalysts which can be used include silica, alumina, titania, silica-titania, zinc oxide, zirconium oxide, gallium oxide, zeolite and rare earth oxides, etc.

These catalysts may be used after being mixed with compounds or supports that are inert with respect to the reaction, or may be used after being supported on such supports. Furthermore, the catalysts may be catalysts that reacted with reaction raw materials or reaction products present in the reaction system. Moreover, the catalysts may be heat-treated beforehand together with reaction raw materials or reaction products.

In cases where a homogenous catalyst is used as a catalyst, the catalyst may be caused to be present in the reaction system by continuously supplying the catalyst to the reaction column; furthermore, in cases where a heterogeneous catalyst is used, the catalyst may be caused to be present in the reaction system by positioning the catalyst inside the reaction column.

In cases where a homogeneous catalyst is continuously supplied to the reaction column, the catalyst may be supplied in the form of a mixture with the dialkyl carbonate and/or aromatic hydroxy compound constituting the reaction raw materials, or may be separately supplied.

Such a reaction of a dialkyl carbonate and aromatic hydroxy compound performed in the presence of a catalyst may be performed in the presence of a solvent if necessary. Solvents which are inert with respect to the reaction may be used as solvents in this case; for example, ethers, aliphatic hydrocarbons or halogenated aromatic hydrocarbons, etc., may be used.

Alternatively, the reaction may also be performed in the presence of a gas, which is inert with respect to the reaction, such as nitrogen, helium or argon, etc.

A reaction apparatus equipped with a distillation column, such as a reaction distillation column or a reaction vessel, which has a distillation column, etc., may be used as a reaction column.

A reaction apparatus, which has a large gas-liquid interface area, so that the aforementioned reaction will tend to shift to the product system side, is desirable for use as a reaction distillation column. In concrete terms, a multi-stage distillation reaction column, which has two or more distillation stages, may be used. A universally known multi-stage distillation column such as a shelf-stage column system, packed column system or combination of a shelf-stage column system and packed column system may be used. In the case of such a multi-stage distillation reaction column, it is desirable that the catalyst be caused to be present in all of the stages. Furthermore, in cases where a solid catalyst is used in a packed column system, this solid catalyst may constitute all or part of the packing material.

In the present invention, aromatic carbonates can be manufactured by performing the aforementioned reactions (1) through (3) using a single reaction column; alternatively, aromatic carbonates can be manufactured using two or more reaction columns. In the present invention, when two reaction columns are used, it is desirable that the aforementioned reaction (1) be formed in the first reaction column, so that mainly alkylaryl carbonates are produced, and that the aforementioned reactions (2) and (3) be performed in the second reaction column, so that diaryl carbonates are produced.

The reaction conditions vary according to the type of reaction apparatus, structure of the reaction apparatus and raw materials used in the reaction, etc.; ordinarily, however, the reaction is performed at a reaction temperature of 50 to 350° C., preferably 100 to 280° C., and more preferably 150 to 280° C. (temperature inside the reaction column). Furthermore, the reaction may be performed under reduced pressure, at ordinary pressure or under pressurization; ordinarily, however, the reaction is performed at a pressure of 2600 Pa to 5.4 MPa. Ordinarily, the mean convection time inside the reaction apparatus is about 0.001 to 50 hours, preferably 0.01 to 10 hours, and more preferably 0.05 to 5 hours.

Furthermore, it is desirable that the above-mentioned dialkyl carbonate and aromatic hydroxy compound be supplied so that the molar ratio (dialkyl carbonate/aromatic hydroxy compound) in the reaction system is in the range of 0.2 to 10, preferably 0.5 to 5.

The dialkyl carbonate and aromatic hydroxy compound may be supplied to the reaction apparatus separately, or may be supplied by the same supply pipe.

The catalyst, calculated in terms of titanium atoms, is used in an amount which is such that the ratio of aromatic polyhydric hydroxy compound to titanium atoms (molar ratio with respect to the aromatic polyhydric hydroxy compound contained in the crude aromatic hydroxy compound) is 2 or greater, and is preferably in the range of 2 to 5. Furthermore, it is ordinarily desirable that the catalyst be used at the rate of 0.0001 to 10 mol %, preferably 0.01 to 5.0 mol %, relative to the hydroxy compound constituting the reaction raw material.

The aromatic carbonate produced by the reaction of the above-mentioned dialkyl carbonate and aromatic hydroxy compound is ordinarily led out from the bottom part of the reaction apparatus. A reaction mixture containing the unreacted raw-material dialkyl carbonate and aromatic hydroxy compound, by-product alkyl aromatic ethers and the catalyst, etc., along with the above-mentioned aromatic carbonate is ordinarily led out from the bottom part of the reaction apparatus.

After the aromatic carbonate is separated from such a reaction mixture and purified, this aromatic carbonate can be used as a raw material in the manufacture of polycarbonates. Such separation and purification can ordinarily be accomplished by distillation.

The unreacted raw materials led out from the bottom part of the reaction apparatus along with the aromatic carbonate can be separated by distillation, recycled and reused.

Furthermore, when aromatic carbonates are manufactured, the reaction is ordinarily performed while by-product alcohols are distilled away from the top part of the reaction apparatus. However, the unreacted dialkyl carbonate, etc., is also led out from the top part of the reaction apparatus along with the by-product alcohols. The unreacted dialkyl carbonate led out from the top part of the reaction apparatus can also be recycled and reused after being purified by separating and distilling away the by-product alcohols, and separating and distilling away the alkyl aromatic ethers.

In cases where the reaction is performed as a continuous operation, the amount of catalyst relative to the aromatic hydroxy compound can easily be controlled if a homogeneous catalyst is used.

In the present invention, the above-mentioned dialkyl carbonate and aromatic hydroxy compound are caused to be present in the reaction system at a molar ratio (dialkyl carbonate/aromatic hydroxy compound) of 0.5 to 2, preferably 0.5 to 1.8. In cases where a distillation column is used as the reaction vessel, this is the molar ratio at the bottom of the column.

In the present invention, it is desirable that the manufacture of aromatic carbonates by means of the above reaction be performed continuously.

The reaction product (aromatic carbonate) produced by the reaction, the by-product alcohols, the unreacted raw materials (dialkyl carbonate and aromatic hydroxy compound) and the by-product alkyl aromatic ethers are led out from the top part and bottom part of the reaction column as reaction mixtures.

In the present invention, after the respective components have been separated from the above-mentioned reaction mixtures, the unreacted raw materials thus obtained can also be recycled into the reaction system and reused.

For example, the aromatic carbonate produced by the reaction is continuously led out from the reaction column; here, this aromatic carbonate is ordinarily led out from the bottom part of the reaction column in liquid form. The aromatic carbonate lead out from the reaction column can then be conducted to a purifying column and purified.

Meanwhile, the by-product alcohols are ordinarily led out from the top part of the reaction column.

Furthermore, the unreacted raw-material dialkyl carbonate and aromatic hydroxy compound can be continuously led out from the reaction column, and can then be separated, recovered and recycled into the reaction system.

In the present invention, when unreacted raw materials are thus recovered and recycled into the reaction system, it is desirable that these unreacted raw materials be recycled into the reaction system after the alkyl aromatic ethers produced as by-products in the reaction column (in the first reaction column when two reaction columns are used) have been separated out by distillation, etc.

In the present invention, aromatic carbonates are manufactured by reacting dialkyl carbonate and aromatic hydroxy compounds under specified conditions. By-product alkyl aromatic ethers can be kept to a low selectivity, and aromatic carbonates can be manufactured at a high yield, so that such aromatic carbonates can be manufactured with good productivity.

WORKING EXAMPLES

Next, the present invention will be concretely described in terms of working examples. However, the present invention is not limited to these working examples.

Working Example 1

An aromatic carbonate was manufactured by a process using the reaction apparatus shown in FIG. 1.

A 500-ml autoclave equipped with a shelf-type distillation column (column height: 3 m, column diameter: 2 inches) in which 40 sieve trays were mounted was used as a methylphenyl carbonate (PMC) production apparatus (reaction apparatus).

The reaction solution was continuously led out from a lead-out pipe installed in the bottom of the autoclave column. After the low-boiling-point components including by-product alcohols were led out from the top part of the distillation column, the components liquefied by means of a condenser were led out of the system, while the remaining components were refluxed in the distillation column (reflux ratio=1). The autoclave and distillation column were heated by electric furnaces, and the temperature at the bottom of the distillation column was controlled to 206° C. The lines supplying the raw materials were also heated by means of heaters.

Initially, phenol (PhOH), bisphenol A and tetraphenoxytitanium Ti(OPh)$_4$ (used as a catalyst) were supplied at the rate of 295.7 g/hour (including 280 g of phenol, 8.2 g of bisphenol A and 7.5 g of catalyst (ratio of bisphenol A to weight of phenol=2.9 wt %, ratio of catalyst to 1 mole of phenol=6×10$^{-3}$ moles, bisphenol A/titanium atoms (molar ratio)=2.0). This mixture was continuously supplied to the 20$^{th}$ stage of the distillation column, and the 20 stages higher than this stage were used as the distillation column.

Dimethyl carbonate (DMC) was continuously supplied to the autoclave at the rate of 1220 g/hour. As a result of an operation performed so that phenol was not distilled out at the top of the column, and so that the DMC/PhOH molar ratio at the bottom of the column was approximately 1, a product was obtained at the rate of 965 g/hour from the top of the distillation column, and at the rate of 549 g/hour from the bottom of the distillation column. The amount of methylphenyl carbonate produced in the solution at the bottom of the column was 94 g/hour, and the amount of anisole produced was approximately 0.3 g/hour.

DMC and methanol (MEOH) were the main components at the top of the column in the initial stage of the reaction, and this mixture contained anisole at the rate of approximately 0.1 g/hour.

Furthermore, the distillation product from the top of the distillation column was distilled at ordinary pressure, and an azeotropic mixture of MeOH and DMC was separated. Afterward, a pure DMC component was produced by further distillation, and this was recycled into the methylphenyl carbonate production apparatus.

Meanwhile, the solution at the bottom of the column in the methylphenyl carbonate production apparatus was concentrated to approximately 710 g/hour by simple distillation. Since DMC was the main component of the low-boiling-point component (approximately 260 g/hour), this was returned to the methylphenyl carbonate production apparatus as recovered DMC, and the concentrated component was supplied to a diphenyl carbonate production apparatus.

In the diphenyl carbonate (DPC) production process, a 500-ml autoclave which had a packed distillation column with a theoretical stage number of 25 stages and an internal diameter of 2 inches was used as the reaction apparatus. A concentrated solution was supplied from an intermediate stage in the distillation column, and a reaction was performed with the pressure at the top of the column set at 110 torr, the temperature at the bottom of the column set at 200° C., the residence time set at 1.5 hours, and the reflux ratio set at 1. The distillation rate from the top of the column was approximately 495 g/hour, and the distillation rate from the bottom of the column was approximately 209 g/hour.

Phenol was the main component of the distillation product from the top of the column; accordingly, this component was returned to the methylphenyl carbonate production process as recycled phenol.

Continuous aromatic carbonate manufacture was performed under the above conditions, and the PMC concentration was evaluated in the initial stage of the reaction, and after 1 and 2 weeks had passed, respectively.

The results obtained are shown in Table 1.

Comparative Example 1

Continuous aromatic carbonate manufacture was performed in the same manner as in Working Example 1, except that bisphenol A was not added as in Working Example 1. The PMC concentration was evaluated in the initial stage of the reaction, and after 1 and 2 weeks had passed, respectively.

The results obtained are shown in Table 1.

Working Example 2

Continuous aromatic carbonate manufacture was performed in the same manner as in Working Example 1, except that the amount of tetraphenoxytitanium Ti(OPh)$_4$ added in Working Example 1 was altered so that the ratio of bisphenol A/titanium atoms (molar ratio) was 3.0. The PMC concentration was evaluated in the initial stage of the reaction, and after 1 and 2 weeks had passed, respectively.

The results obtained are shown in Table 1.

Working Example 3

Continuous aromatic carbonate manufacture was performed in the same manner as in Working Example 1, except that the amount of tetraphenoxytitanium Ti(OPh)$_4$ added in Working Example 1 was altered so that the ratio of bisphenol A/titanium atoms (molar ratio) was 4.0. The PMC concentration was evaluated in the initial stage of the reaction, and after 1 and 2 weeks had passed, respectively.

The results obtained are shown in Table 1.

Working Example 4

Continuous aromatic carbonate manufacture was performed in the same manner as in Working Example 1, except that the amount of tetraphenoxytitanium Ti(OPh)$_4$ added in Working Example 1 was altered so that the ratio of bisphenol A/titanium atoms (molar ratio) was 5.0. The PMC concentration was evaluated in the initial stage of the reaction, and after 1 and 2 weeks had passed, respectively.

The results obtained are shown in Table 1.

TABLE 1

| | PMC Concentration (%) | | | | |
| --- | --- | --- | --- | --- | --- |
| Reaction Time | Working Example 1 | Comparative Example 1 | Working Example 2 | Working Example 3 | Working Example 4 |
| BPA/Ti (molar ratio) | 2 | 0 | 3 | 4 | 5 |
| Initial stage of reaction | 17.2 | 17.1 | 17.3 | 17.2 | 17.3 |
| After 1 week | 17.1 | 17 | 17.1 | 17.3 | 17.2 |
| After 2 weeks | 17.1 | 17 | 17.1 | 17.1 | 17.3 |

Even in a case where bisphenol A, which is an aromatic polyhydric hydroxy compound, was contained at the rate of 2.9 wt % relative to 1 mole of phenol, a PMC concentration comparable to that obtained in a comparative example in which no bisphenol A was added was stably obtained over a long period of time.

Figure 1:
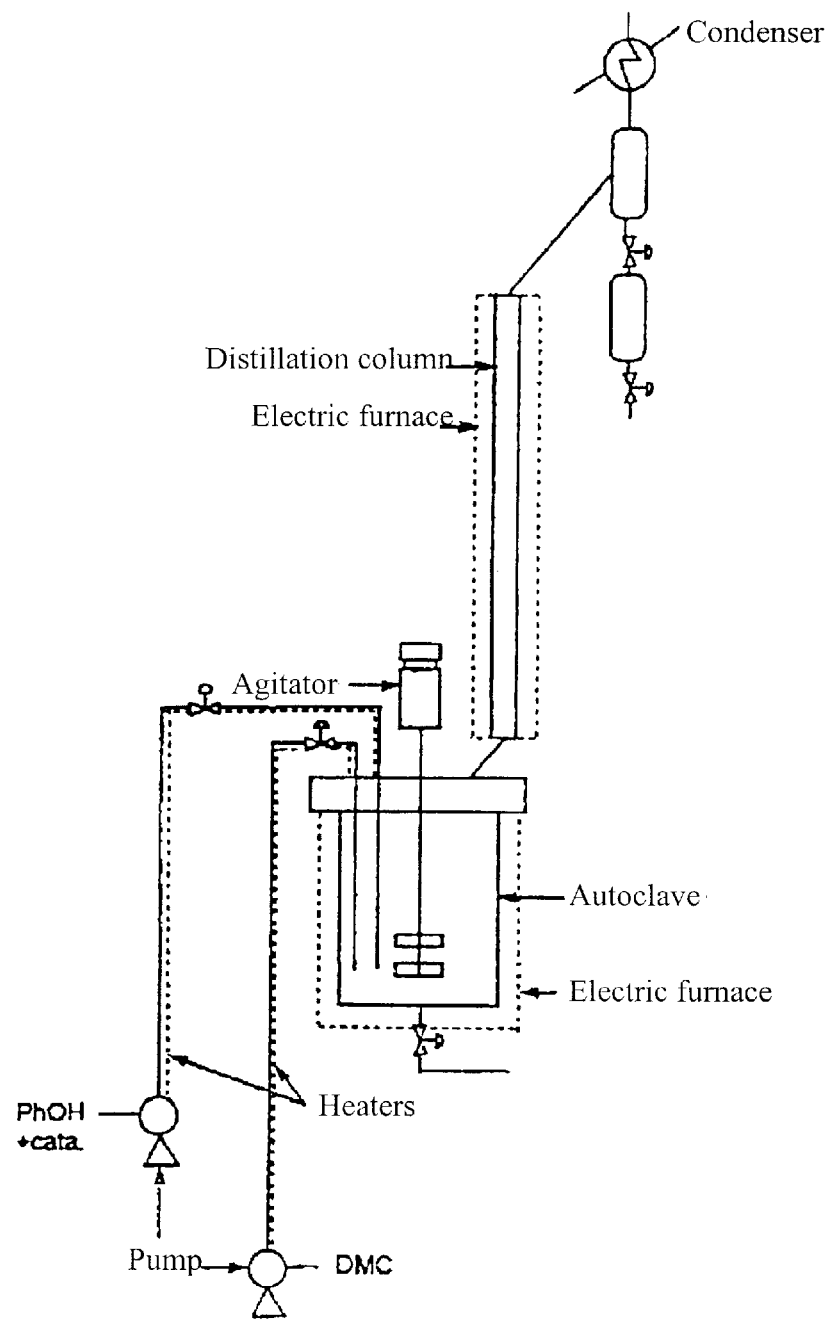
FIG. 1 is a schematic diagram of the reaction apparatus used in the working examples.

What is claimed is:

1. A method for manufacturing aromatic carbonates, comprising reacting a dialkyl carbonate and an aromatic hydroxy compound in the presence of a catalyst to produce aromatic carbonates while distilling off by-product alcohols and by-product dialkyl carbonates from a reaction system, wherein:

(i) the aromatic hydroxy compound is a crude compound mixture which comprises an aromatic hydroxy compound and 0.5 to 10 wt % of an aromatic polyhydric hydroxy compound, (ii) a titanium compound expressed by TiX$_3$ or TiX$_4$ (here, X indicates a halogen atom, an acetoxy group, an alkoxy group or an aryloxy group) is used as the catalyst, and (iii) when the catalyst is calculated in terms of titanium atoms, the amount of catalyst used is an amount that satisfies the following relationship with respect to the aromatic polyhydric hydroxy compound contained in the aromatic hydroxy compound:

aromatic polyhydric hydroxy compound / titanium atoms (molar ratio)>2.

2. The method for manufacturing aromatic carbonates according to claim 1, wherein the amount of the aromatic polyhydric hydroxy compound that is contained in the crude aromatic hydroxy compound is in the range of 0.5 to 2.0 wt %.

3. The method for manufacturing aromatic carbonates according to claim 1, wherein the aromatic hydroxy compound is phenol.

4. The method for manufacturing aromatic carbonates according to claim 1, wherein the aromatic polyhydric hydroxy compound is bisphenol A.

5. The method for manufacturing aromatic polycarbonates according to claim 1, wherein the crude compound mixture comprises compounds obtained by purifying the aromatic hydroxy compounds produced as by-products in the manufacture of a polycarbonate.

6. The method for manufacturing aromatic carbonates according to claim 3, wherein the aromatic polyhydric hydroxy compound is bisphenol A.

7. The method for manufacturing aromatic carbonates of claim 1, wherein the molar ratio of aromatic polyhydric hydroxy compound to titanium atoms is 2 to 5.

* * * * *